United States Patent
Rizzo et al.

(10) Patent No.: US 6,394,808 B2
(45) Date of Patent: May 28, 2002

(54) PROSTHETIC DEVICE FOR INTRAOSSEOUS DENTAL IMPLANTS

(75) Inventors: Rosario Rizzo, Gussago; Giuseppe Bellandi, Roncadelle, both of (IT)

(73) Assignee: Physioplant S.R.L. (IT)

( * ) Notice: Subject to any disclaimer, the term of this patent is extended or adjusted under 35 U.S.C. 154(b) by 0 days.

(21) Appl. No.: 09/849,004

(22) Filed: May 7, 2001

(30) Foreign Application Priority Data

May 10, 2000 (IT) .............................. BS2000 A 000046

(51) Int. Cl.[7] .................................................. A61C 8/00
(52) U.S. Cl. ........................ 433/173; 433/169; 433/172
(58) Field of Search .................................. 433/172, 173, 433/174, 175, 176, 169

(56) References Cited

U.S. PATENT DOCUMENTS

| | | | | |
|---|---|---|---|---|
| 4,568,285 A | * | 2/1986 | Chiaramonte et al. | 433/173 |
| 4,636,216 A | * | 1/1987 | Tatum | 433/173 |
| 5,030,095 A | * | 7/1991 | Niznick | 433/173 |
| 5,040,982 A | * | 8/1991 | Stefan-Dogar | 433/169 |
| 5,674,072 A | * | 10/1997 | Moser et al. | 433/173 |
| 5,678,995 A | * | 10/1997 | Kirsch et al. | 433/172 |
| 5,961,328 A | * | 10/1999 | Somborac et al. | 433/173 |

\* cited by examiner

*Primary Examiner*—John J. Wilson
(74) *Attorney, Agent, or Firm*—McGlew and Tuttle, P.C.

(57) ABSTRACT

A prosthetic device for intraosseous dental implants includes an intraosseous support implant (11) and an intraplantar pin (12). The support implant (11) has a blind cavity (18) open towards its top and with at least one internal zone having a conical surface (20). The intraplantar pin (12) has a shank (21) which is intended to be implanted in the cavity of the implant and a transmucosa connection head (22) lying above the implant. The shank (21) has at least one conical external zone (23) of forced coupling with the conical internal zone (20) of the cavity of the support implant.

9 Claims, 1 Drawing Sheet

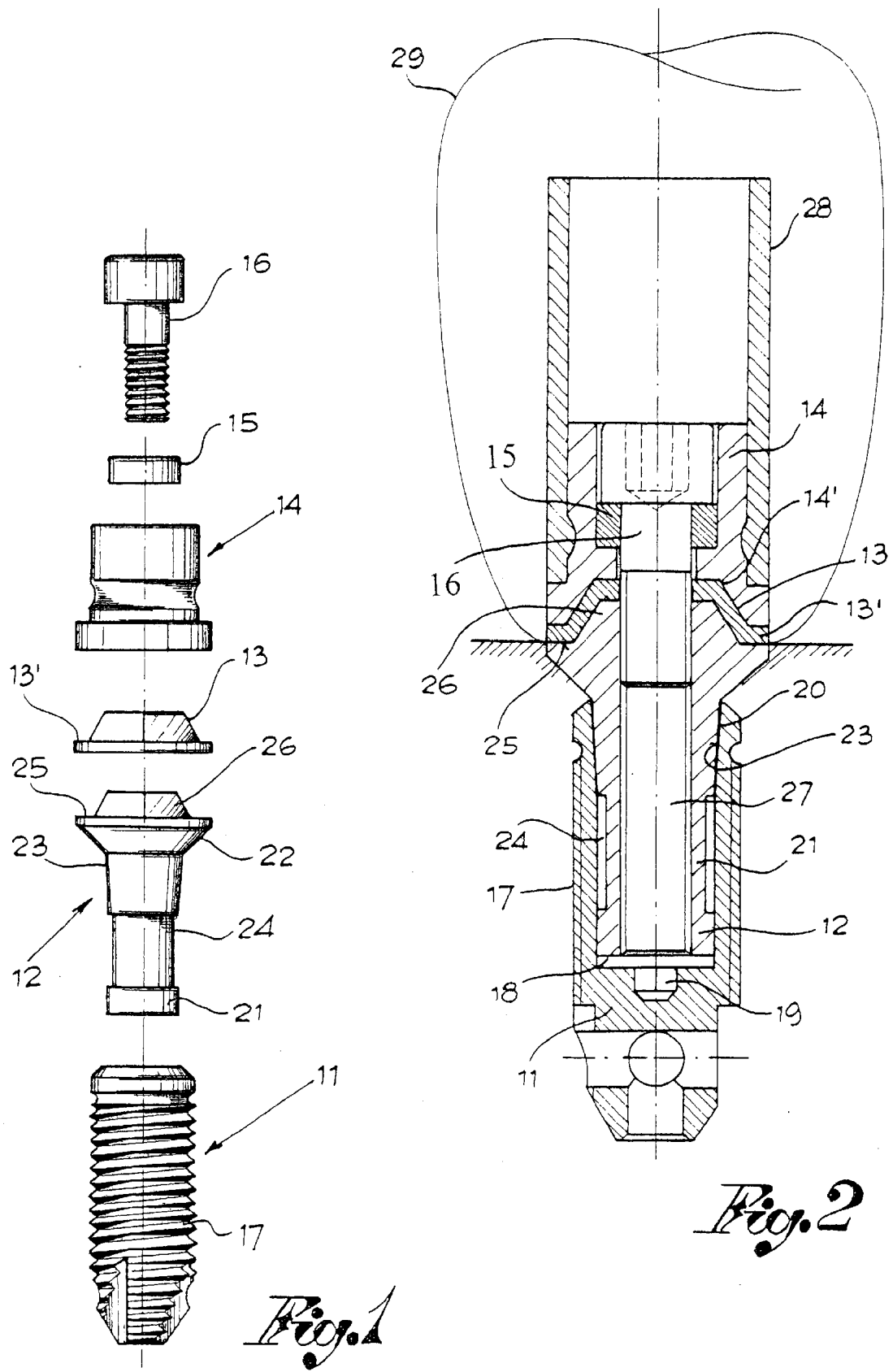

PROSTHETIC DEVICE FOR INTRAOSSEOUS DENTAL IMPLANTS

FIELD OF THE INVENTION

The present invention pertains to intraosseous dental implants and more specifically to a prosthetic device for such implants.

BACKGROUND OF THE INVENTION

Intraosseous or osteointegrated dental implants usually comprise an implant (fixture), which is implanted in the bone in order to be integrated with it, and a prosthetic intraplantar pin having a transmucosa connection (abutment), to which the dental prosthesis is fixed. Currently, if it is used, the intraplantar pin is screwed and/or cemented directly in the implant with a male/female coupling in order to thus form a complete integral unit. However, this mode of fixation of the intraplantar pin poses many problems.

In fact, if the pin is simply screwed, given the forces to which the prosthesis is subjected, the pin tends to unscrew with the result of making possible rotational movements and even accidental disconnections of the prosthesis which then require interventions for repairing the fixation. In other words, the stability of the prosthesis may be precarious. On the other hand, if the pin is cemented, it becomes difficult to remove. In both cases then, such a fixation makes the search for parallelization of the elements difficult, and moreover, the resulting composition is highly rigid both in terms of its structure and in terms of its behavior under force, conditions which may cause damage to the bone and which, at any rate, do not correspond to the elastic, or cushioned, connection, as exists between a natural tooth and bone.

SUMMARY AND OBJECTS OF THE INVENTION

The object of the present invention is to eliminate or at least to reduce the above mentioned problems mainly by means of:

- the search for a balance between stability and reversibility of the fixation, so as to ensure both with elements of a novel and original combination;
- the achievement of a paraphysiological, "cushioned" dental prosthesis, which reproduces the characteristics of a connection between a natural tooth and bone so as not to stress and damage the bone;
- the elimination of rotational movements and/or of accidental disconnections to reduce the need for repair interventions;
- ease of insertion of bridge-type prostheses even for unparallel implants up to 60°;
- ease and precision of the taking of impressions by means of so-called "copying pick-up," in the absence of a "pulling effect" of the impression;
- reduction in the lateral tensile forces typical of the rigid systems both on the "fixture" and on the components of the prosthesis, the tightening screw in particular, thanks to the cushioning and to the washer made of plastic material;
- the easy removability of the intraplantar pin by means of a screw-type extractor coaxial to the implant.

This object is accomplished with a prosthetic device for intraosseous dental implants comprising an intraosseous support implant and an intraplantar pin. The support implant has a blind cavity, which is open towards the top of the implant and has at least one internal zone with a conical surface. The intraplantar pin has a shank intended to be implanted and to be blocked in the cavity of the support implant and a transmucosa connection head lying above the implant. The shank has at least one conical external zone of forced coupling with the conical internal zone of the cavity of the support implant. A cap for a dental prosthesis is fixed to the connection head with the interposition of a semirigid cushioning ring.

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which a preferred embodiment of the invention is illustrated.

BRIEF DESCRIPTION OF THE DRAWINGS

In the drawings:

FIG. 1 is a side view of the separated components of the device; and

FIG. 2 is a longitudinal sectional view of the assembled device.

DESCRIPTION OF THE PREFERRED EMBODIMENT

Referring to the drawings in particular, the prosthetic device essentially comprises an intraosseous implant 11, which is commonly called a "fixture," an intraplantar pin 12, which is also called an "abutment," a cushioning ring 13, a cap 14 for a dental prosthesis, a washer 15 and a fastening screw 16.

The intraosseous implant 11, the intraplantar pin 12, the fastening screw 16, and the cap 14 may all be made of titanium or another suitable material that is usually used in the field of dentistry. The cushioning ring 13 and the washer 15 may be made of a biocompatible semirigid material.

In particular, the intraosseous implant 11, which is basically cylindrical, has, externally, at least one threaded or furrowed part 17 and, internally, it has an axial cavity 18, which is open at the top of the implant, and a bottom that is provided with a central hexagonal hole 19. The axial cavity 18 has at least one conical zone 20 in the proximity of its mouth. The bottom hexagonal hole 19 is used to engage, with a tool, the implant for its seated installation in a bone prepared in advance.

The intraplantar pin 12 has a shank 21 and a connection head 22. The shank 21 is shaped to be accommodated in the axial cavity 18 of the intraosseous implant 11 and thus has at least one of its external zones 23 intended to be joined complementarily and tightly to the conical internal zone 20 of the implant 11. The shank 21 can additionally have one or more external steps 24 to facilitate the fixation by means of cementing, if desired, between the implant and the pin.

The intraplantar pin 12 is to remain fixed in the intraosseous implant 11 exclusively via the axial coupling of the respective conical zones 13, 20, and the optional cementing only represents a supplemental fixation.

The head 22 of the pin 12, when same is inserted into the intraosseous implant 11, is above the implant proper, forming a transmucosa connection. It extends conically starting from the shank 21 and then has a re-entry, which defines a shoulder 25, which is turned upwards, from which rises a portion 26 having the shape of a truncated pyramid, truncated cone, or the like.

Axially, the intraplantar pin 12 is passed through along its entire length by a threaded hole 27, which is used both for screwing an extractor (not shown) thereto for extracting the pin 12 from the implant 11 and for screwing the fastening screw 16 thereto as appears evident below.

The cushioning ring 13 is shaped like a truncated pyramid-shaped or upside-down truncated cone-shaped cup for being joined to the truncated-pyramid-shaped or truncated-cone-shaped portion 26, covering same, and resting with a peripheral flange 13' on the shoulder 25 at the base of the truncated-pyramid-shaped portion of the head of the pin 12. The cap 14 is then arranged above the cushioning ring 13, has a basic notch 14', which is joined to the ring and is fixed in place by means of the fastening screw 16 which is screwed into the axial hole 27 of the pin 12 as shown in FIG. 2. The head of the fastening screw is embedded in the cap and acts on same with the interposition of the washer 15.

A calcinable element 28 applied to the cap and a dental prosthesis 29 is also shown in FIG. 2 of the drawing.

In practice, the support implant 11 is implanted in the bone to become integrated with same progressively, and subsequently, the intraplantar pin is inserted into the cavity 18 of the implant, at which it is blocked by means of the conical coupling 20, 23. Then, the cushioning ring 13 and the cap 14 are mounted by fixing them on the connection head of the pin by means of the fastening screw. Within the framework of the composition, the cushioning ring 13, thanks to its relative elasticity, permits the final prosthesis elastic movements, without directly loading the bone and basically reproducing conditions similar to those of a connection between a natural tooth and bone.

While a specific embodiment of the invention has been shown and described in detail to illustrate the application of the principles of the invention, it will be understood that the invention may be embodied otherwise without departing from such principles.

What is claimed is:

1. An intraosseous dental implant prosthetic device comprising:
   an intraosseous support implant with a blind cavity, which is open towards the top of the implant and has at least one internal zone with a conical surface; and
   an intraplantar pin with a shank to be implanted and to be blocked in the cavity of the support implant and with a transmucosa connection head lying above the implant and extending from the shank and narrowing to form an annular shoulder facing upwards, the transmucosa connection head ending above the shoulder with a truncated-pyramid-shaped or truncated-cone-shaped portion, the shank having at least one conical external zone of forced coupling with the conical internal zone of the cavity of the support implant;
   a semirigid cushioning ring; and
   a cap for a dental prosthesis fixed to the connection head with the interposition of the semirigid cushioning ring.

2. A prosthetic device for dental implants in accordance with claim 1, wherein the connection head of the intraplantar pin extends conically from the shank and then narrows to form the annular shoulder, the cushioning ring having a complementary truncated-pyramid or truncated-cone shape to be joined to and to cover the portion of the connection head, and they have a peripheral flange resting on the annular shoulder.

3. A prosthetic device in accordance with the claim 2 wherein the intraplantar pin is passed through axially by a threaded hole, the cap for the dental prosthesis being fixed to the intraplantar pin with an axial screw screwed into the threaded hole, with a washer being placed between the head of the screw and the cap.

4. A prosthetic device in accordance with claim 2, wherein the blind cavity of the support implant has a hexagonal hole on its bottom.

5. A prosthetic device in accordance with the claim 1 wherein the intraplantar pin is passed through axially by a threaded hole, the cap for the dental prosthesis being fixed to the intraplantar pin with an axial screw screwed into the threaded hole, with a washer being placed between the head of the screw and the cap.

6. A prosthetic device in accordance with claim 1, wherein the blind cavity of the support implant has a hexagonal hole on its bottom.

7. An intraosseous dental implant prosthetic device comprising:
   an intraosseous support implant with a blind cavity, which is open towards the top of the implant and has at least one internal zone with a conical surface; and
   an intraplantar pin with a shank to be implanted and to be blocked in the cavity of the support implant and a transmucosa connection head lying above the implant, the shank having at least one conical external zone of forced coupling with the conical internal zone of the cavity of the support implant, a cap for a dental prosthesis being fixed to the connection head with the interposition of a semirigid cushioning ring, wherein the connection head of the intraplantar pin extends conically from the shank, and then narrows, forming an annular shoulder turned upwards, and ends, above the shoulder, with a truncated-pyramid-shaped or truncated-cone-shaped portion, with the cushioning ring having a complementary truncated-pyramid or truncated-cone shape to be joined to and to cover the portion of the connection head, and they have a peripheral flange resting on the annular shoulder.

8. A prosthetic device in accordance with the claim 7 wherein the intraplantar pin is passed through axially by a threaded hole, the cap for the dental prosthesis being fixed to the intraplantar pin with an axial screw screwed into the threaded hole, with a washer being placed between the head of the screw and the cap.

9. A prosthetic device in accordance with claim 7, wherein the blind cavity of the support implant has a hexagonal hole on its bottom.

* * * * *